United States Patent [19]
Matsunaga

[11] Patent Number: 5,422,567
[45] Date of Patent: Jun. 6, 1995

[54] HIGH FREQUENCY POWER MEASUREMENT

[75] Inventor: Derek Matsunaga, Boulder, Colo.

[73] Assignee: Valleylab Inc., Boulder, Colo.

[21] Appl. No.: 174,593

[22] Filed: Dec. 27, 1993

[51] Int. Cl.$^6$ .............................................. A61B 17/39
[52] U.S. Cl. .................................... 324/142; 364/483; 606/38; 606/40
[58] Field of Search .................... 606/38, 40; 364/483; 324/142

[56] References Cited

U.S. PATENT DOCUMENTS

| | | |
|---|---|---|
| 3,486,115 | 12/1969 | Anderson .............................. 364/483 |
| 3,601,126 | 1/1969 | Estes . |
| 4,092,986 | 6/1978 | Schneiderman . |
| 4,102,341 | 7/1978 | Ikuno et al. . |
| 4,281,373 | 7/1981 | Mabille . |
| 4,321,926 | 3/1982 | Roge . |
| 4,372,315 | 2/1983 | Shapiro et al. . |
| 4,658,819 | 4/1987 | Harris et al. . |
| 4,727,874 | 3/1988 | Bowers et al. . |
| 4,860,745 | 8/1989 | Farin et al. . |
| 4,922,210 | 5/1990 | Flachenecker et al. . |
| 4,969,885 | 11/1990 | Farin . |

*Primary Examiner*—Kenneth A. Wieder
*Assistant Examiner*—Mark Wardas
*Attorney, Agent, or Firm*—Peter C. Richardson; Lawrence C. Akers; Aaron Passman

[57] ABSTRACT

A monitoring circuit for an electrosurgical generator has active and return output conductors. Voltage, current and the inverse of current picked up inductively are provided to a adder circuits for summing the picked up voltage and current and computing the difference of the picked up voltage and the current. Root mean square to direct current converters signal RMS average values of the sum and difference. A microprocessor squares the values and applies them to a formula wherein the sum signals have subtracted therefrom the difference signals; the results are divided by four to provide the root mean square of the power applied to the load. During desiccation the output is regulated in response to impedance to shut off output. A diagnostic circuit relates impedance load and output response during operation to a look up table or a microprocessor algorithm to calibrate. Feedback modifies the output when the adders determine the power applied to the load in real time. A method has generator output to active and return conductors and to inductive pick ups for voltage and current, computes sum and differential values, changes root mean square to direct currents, squares the values and subtracts the differential from the summation then divides the result finding the root mean square value of the power.

20 Claims, 1 Drawing Sheet

HIGH FREQUENCY POWER MEASUREMENT

FIELD OF THE INVENTION

A high frequency power monitoring circuit for an electrosurgical generator applied to a load to achieve an electrosurgical effect calculates the power with an adder circuit to the value of the actual power applied to the load without any capacitance such as would have been introduced by cables of varying lengths or the effects of circuit components resulting from the application of high frequency energy thereto.

BACKGROUND OF THE DISCLOSURE

This electrosurgical circuit monitors power consumed at the electrodes and establishes a power measurement independent of capacitance such that cables of preset impedance and the effects of high frequency current on multipliers presently used in such circuits are eliminated. It has been found that the use of certain circuit elements that are more stable give values for power consumed which when mathematically applied provide the exact power measurement of the electrosurgical generator under varying loads.

Capacitively loaded circuits, i.e. an electrosurgical generator with long leads, or laparoscopic electrosurgical instruments that capacitively couple with the trocar or other instruments, e.g. endoscopes, video etc., are difficult to accurately regulate and automatically control since the impedance signals are subject to the effects of capacitive and inductive sensitive components. In particular, multipliers and/or phase detectors introduce spurious signal abnormalities which are difficult to design out and compensate for. Because of the capacitance of long leads for high frequency power transmission, the assumption that the root mean square of voltage and current can be multiplied for accurate power determination is false. The current divider effect introduced by the leads, particularly, those which are long, results in the current at the electrosurgical generator output being unequal to the current through the load, i.e. the patient's tissue. Moreover, the variation of the tissue impedance of the patient is not approximated by the output current and to measure the voltage and current delivered at the electrodes is impractical. The multiplied root mean square values of voltage and current to obtain power are inaccurate, subject to circuit component values and tend to drift over time and are unstable at the high frequencies typically used in electrosurgery. Specifically, the phase angle between the voltage wave form and current wave form must be taken into account. Traditionally, the root mean square values of voltage and current are multiplied together and further multiplied by the cosine of the unknown phase angle. Since the phase angle is not readily available and not easily measured, no accurate way of applying the cosine of the phase angle to a control the operation of an electrosurgical generator is possible. A means to account for the phase angle and any changes thereof is not appreciated or understood. A way to circumvent the problem with a circuit that is insensitive to component capacitance is required.

U.S. Pat. No. 4,922,210 has a control for the driver circuit of a high frequency electrosurgical generator that is responsive to a resultant signal which is obtained by adding a voltage signal and an inverse current signal from the output of the electrosurgical generator. U.S. Pat. No. 4,922,210 has a positive feedback high frequency oscillator with a complementary power amplifier that derives part of input from parallel resonant circuit voltage and the remainder from series resonant circuit current. The oscillator included a voltage feedback means, current inverse feedback means, algebraic addition means and pulse converting means. No apparent recognition of the problems of inaccuracies introduced by capacitive sensitive components are noted and the measurements applied to determine the power actually delivered to the load are not correct.

As a result of manual operation problems, several attempts to provide automatic generator operation when surgical forceps contact patient tissue have been patented.

U.S. Pat. No. 3,601,126 has the amplitude of the current flowing through an electrosurgical circuit monitored and compared with a reference amplitude so that it is regulated in response to the amplitude and therefore indirectly with respect to the tissue load. In connection with desiccation in a bipolar electrosurgical system U.S. Pat. No. 4,092,986 has circuitry to reduce the output current in accordance with increasing load impedance. Therein voltage output is maintained constant while the current is decreased with increasing load impedance.

U.S. Pat. No. 4,281,373, has a DC voltage k $nV_S$ proportional to the output AC voltage which is subtracted from the sum of a fixed voltage $V_R$ and a voltage $rI_S$ proportional to the current flowing through the utilization circuit, to produce a voltage that is amplified and then used to act on the chopping supply that excites the power oscillator 5. The '373 patent does not rely on a comparison between an actual output voltage and a reference voltage to control the output voltage, but rather by adding a positive feedback it tends to raise the output voltage as the current in the utilization circuit increases.

U.S. Pat. No. 4,321,926 has a feedback system to control dosage with impedance sensing. U.S. Pat. No. 4,372,315 discloses a circuit which measures impedances after delivering a set number of radio frequency pulses on a pulse burst by pulse burst basis. U.S. Pat. No. 4,658,819 discloses a circuit wherein the power delivered to the electrode is a function of the voltage from a DC supply and the load as measured by sensors of load voltage and current. A microprocessor controller digitizes the sensing signals and computes the load impedance and actual power being delivered. The microprocessor controller accordingly repeats the measurement, calculation and correction process approximately every 20 milliseconds as long as the generator is operating.

U.S. Pat. No. 4,727,874 discloses an electrosurgical generator having high frequency pulse width modulated feedback power control. Analysis of parts of high frequency signals to determine the effects of impedance loads on the electrosurgical unit are taught. U.S. Pat. No. 4,860,745 discusses the problems encountered when turning off radio frequency power based upon measurements of the time derivative of patient tissue impedance and, instead, presents a circuit which turns off generator radio frequency power based upon fixed fractional changes in the amount of radio frequency current delivered to the patient tissue during desiccation or based upon generator sparking and harmonic frequency generation. U.S. Pat. No. 4,969,885 discloses a high frequency surgery device for cutting and/or coagulating biological tissue. In the '885 patent a blocking capacitor on the active output of the isolation transformer has its sensor positioned in the circuit after a capacitor and an output voltage comparison to a desired voltage and feedback for automatic adjustment. The '885 patent has a direct response solely to variation of a measure of the actual output voltage, for control of the energization of the power amplifier that delivers that actual output voltage. U.S. Pat. No. 4,102,341 seeks to monitor the relative difference between the current $I_A$ which flows to the knife electrode and current $I_P$ which is the current which goes to (or comes from) the patient, this difference is due to stray current. In order to do this, a voltage divider 22 is provided from which the quotient $I_A/I_P$ is provided as an output which is displayed on an instrument 23. This is a problem different from those which are involved in the effects of fluctuation of the applied high frequency voltage and monitoring a display or providing alarms relating solely to variations in applied voltage.

The foregoing references include disclosures of load responsive electrosurgical generators which are regulated as a function of the tissue being treated. The references are incorporated by reference and made a part hereof.

SUMMARY OF THE INVENTION

A high frequency power monitoring circuit for an electrosurgical generator applied to a load to achieve an electrosurgical effect may have a source of high frequency electrosurgical energy including an electrosurgical generator and its active and return conductors connected to the output thereof. An inductive pick up for voltage is preferably connected between the conductors of the electrosurgical generator. An inductive pick up for current flowing through at least one of the conductors of the output from the electrosurgical generator and an inductive pick up for the inverse of current flowing through the one conductor of the electrosurgical generator output are preferred.

A first adder circuit for computing the instantaneous inductively picked up voltage with the instantaneously inductively picked up current may provide a sum indicative instantaneously thereof. A second adder circuit for computing the inductively picked up voltage and the inverse of the instantaneously derived current may provide a differential value thereof. A root mean square to direct current converter for the summation value most preferably provides a signal of the instantaneous value of the summation as a root mean square summation value. A root mean square to direct current converter for the differential value may provide a signal of the instantaneous value of the differential as a root mean square differential value.

A microprocessor periodically receives the root mean square summation and root mean square differential values and squares those root mean square summation and differential values for application to a formula so preferably the squared root mean square summation values have subtracted therefrom the squared root mean square differential values so the result therefrom may be divided by four to provide the root mean square value of the actual power applied to the load.

The root mean square to direct current converter for the summation value and the root mean square to direct current converter for the differential value are preferably each inputs to a microcontroller with band limited signal processing capabilities. The length and impedance of the active and return conductors are insignificant to the determination of the root mean square value of the actual power applied to the load.

A feedback circuit is preferably connected to the electrosurgical generator for modifying the output thereof. The first and second adders may determine the root mean square value of the actual power applied to the load in real time so the microprocessor may periodically receive the squared root mean square summation and subtract the squared root mean square differential values so the result therefrom may be divided by four to provide an indication of load for use in the feedback circuit to control the output of the electrosurgical generator.

The inductive pick up for current flowing through at least one of the conductors of the output from the electrosurgical generator is preferably located along the active conductor or the return conductor. The inductive pick up for the inverse of current flowing through the one conductor of the electrosurgical generator output is preferably located along the active or return conductors. The electrosurgical generator may have an internal diagnostic circuit which relates impedance load and output response during operation to a look up table or an algorithm programmed in the microprocessor for obtaining a correction to automatically calibrate the response and operation of the high frequency power monitoring circuit.

A self-operating desiccation regulator may be connected to the electrosurgical generator output to in response to impedance shut off output when the impedance is at a level preset in the microprocessor. An inductive pick up for voltage between the active and the return conductors is connected to a root mean square to direct current converter for the voltage to preferably provide a measure of the root mean square of the voltage and the microprocessor may be programmed to find the phase angle between voltage and current. An inductive pick up for voltage between the active and return the conductors is preferably connected to a root mean square to direct current converter for the voltage to provide a measure of the root mean square of the voltage and the microprocessor may be programmed to find the length of a controlled capacitance cable.

A method for monitoring high frequency power from an electrosurgical generator applied to a load to achieve an electrosurgical effect with the step of connecting an electrosurgical generator output to active and return conductors. The further step of connecting an inductive pick up for voltage between the conductors of the electrosurgical generator may be included. Another step of connecting an inductive pick up for current flowing through at least one of the conductors of the output from the electrosurgical generator is preferred. The method may have an added step of connecting an inductive pick up for the inverse of current flowing through the one conductor of the electrosurgical generator output. It is preferred that a step of computing with a first adder circuit the instantaneous inductively picked up voltage with the instantaneously inductively picked up current to provide a sum indicative instantaneously thereof follows. The additional step of computing with a second adder circuit the inductively picked up voltage and the inverse of the instantaneously derived current providing a differential value thereof may be included. Converting a root mean square to direct current for the summation value to provide a signal of the instantaneous value of the summation as a root mean square summation value is preferred as another step. Then the step of converting a root mean square to direct current for the differential value to provide a signal of the instantaneous value of the differential as a root mean square differential value is preferably performed. Thereafter, the step of receiving in a microprocessor periodically the root mean square summation and root mean square differential values may be employed. The method then may include the step of squaring those root mean square summation and differential values for application to a formula wherein the squared root mean square summation values have subtracted therefrom the squared root mean square differential values. Finally, the step of dividing the result therefrom by four to provide the root mean square value of the actual power applied to the load is followed.

The step of applying the root mean square to direct current converter for the summation and differential values to a microcontroller with band limited signal processing capabilities is preferred. The step of determining the root mean square value of the actual power applied to the load independently of the length and impedance of the active and return conductors is also preferred. Then the steps of connecting a feedback circuit to the electrosurgical generator for modifying the output thereof and determining with the first and second adders the root mean square value of the actual power applied to the load in real time so the microprocessor can periodically receive and square the root mean square summation and subtract the squared root means square differential values and thereafter calculate in the formula so the result therefrom can be divided by four to provide an indication of load for use in the feedback circuit to control the output of the electrosurgical generator may be followed.

The method may have the step of locating the inductive pick up for current flowing through at least one of the conductors along the active conductor or the return conductor. The step of locating the inductive pick up for the inverse of current flowing through at least one of the conductors along the active conductor or the return conductor is preferably performed. The step of providing in the electrosurgical generator an internal diagnostic circuit which relates impedance load and output response during operation to a look up table or an algorithm programmed in the microprocessor for obtaining a correction to automatically calibrate the response and operation of the high frequency power monitoring circuit is performed. The step of connecting a self-operating desiccation regulator to the electrosurgical generator output to in response to impedance shut off output when the impedance is at a level preset in the microprocessor may follow. The steps of connecting an inductive pick up for voltage between the active and return the conductors to a root mean square to direct current converter for the voltage and thereby providing a measure of the root mean square of the voltage and the microprocessor is programmed for finding the phase angle between voltage and current may perhaps come thereafter. The steps of connecting an inductive pick up for voltage between the active and return the conductors to a root mean square to direct current converter for the voltage and thereby providing a measure of the root mean square of the voltage and the microprocessor is programmed for finding the length of a controlled capacitance cable may be a part of the preferred method.

DETAILED DESCRIPTION OF THE INVENTION

Figure 1:
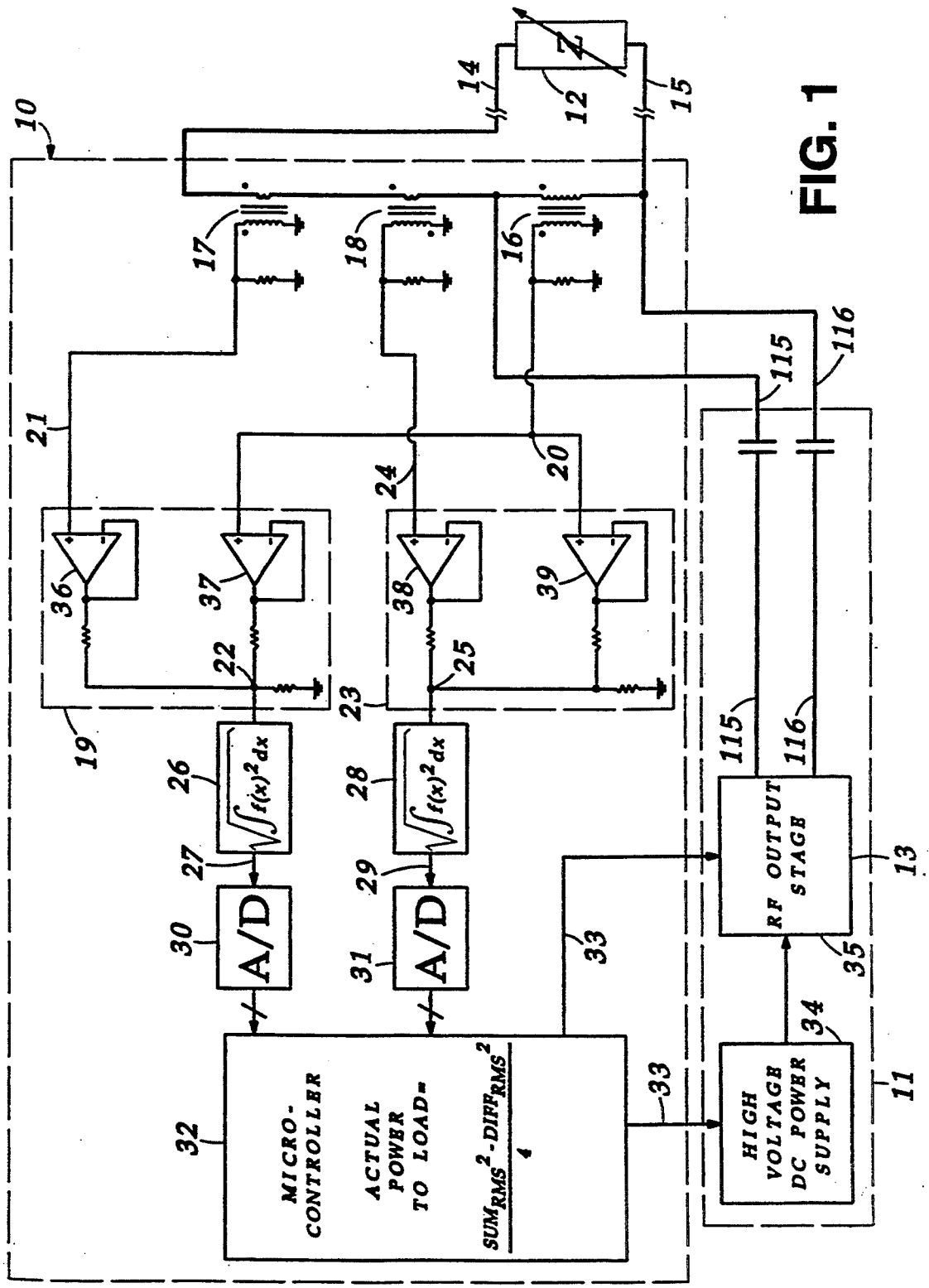
FIG. 1 is a schematic diagram with blocks to represent the components of a high frequency power monitoring circuit for an electrosurgical generator shown applied to a load to achieve an electrosurgical effect.

A high frequency power monitoring circuit 10 for an electrosurgical generator 11 applied to a load 12 to achieve an electrosurgical effect has a source of high frequency electrosurgical energy 13 as part of the electrosurgical generator 11 to supply its active and return conductors 14 and 15, respectively, connected to receive the output therefrom. An inductive pick up 16 for voltage is connected between the active and return conductors 14 and 15, respectively, of the electrosurgical generator 11. The high frequency power monitoring circuit 10 can be internal to the electrosurgical generator 11, i.e., within the circuitry thereof or alternatively externally attached thereof. An inductive pick up 17 for current flowing through at least one of the active or return conductors 14 or 15, respectively, of the output from the electrosurgical generator 11. It is preferred to use the active conductor 14 for each pick up. An inductive pick up 18 for the inverse of current flowing through the one active or return conductor 14 or 15 of the electrosurgical generator 11 output provide input to the high frequency monitoring circuit 10. It is preferred to use the active conductor 14 for that pick up.

A first adder circuit 19 for computing the instantaneous inductively picked up voltage 20 with the instantaneously inductively picked up current 21 provides a sum indicative instantaneously thereof 22. A second adder circuit 23 for computing the inductively picked up voltage 20 and the inverse of the instantaneously derived current 24 provides a differential value 25 indicative instantaneously thereof. A root mean square to direct current converter 26 for the summation value 22 provides a signal 27 of the instantaneous value of the summation as a root mean square summation value. A root mean square to direct current converter 28 for the differential value 25 provides a signal 29 of the differential value as a root mean square value.

Analog to digital converters 30 and 31 are in the high frequency monitoring circuit 10 to convert analog input voltages 27 and 29 into digital words as the outputs therefrom. It can be a discrete converter or integrated into a microprocessor 32. The microprocessor 32 can be a microcontroller by which the electrosurgical generator 11 output to the conductors 14 and 15 for an electrosurgical effect is controlled. The microprocessor 32 or microcontroller 32 accepts the SUM$_{rms}$ and DIFF$_{rms}$ values 27 and 29 from the analog to digital converters 30 and 31 and subsequently makes the power calculation. The results from the power calculation may preferably be used in a closed loop 33 control of the high voltage DC power supply 34 or alternatively the output stage 35 of the electrosurgical generator 11.

The microprocessor 32 periodically receives the root mean square summation and root mean square differential values 27 and 29, respectively, and squares those root mean square summation and differential values for application to a formula so the squared root mean square summation values can then have subtracted therefrom the squared root mean square differential values. The resulting difference therefrom is divided by four to provide the root mean square value of the actual power applied to the load 12. The actual power applied to the load 12 is of significance as it can be used to control the output of the electrosurgical generator 11 in accord with the instantaneous needs of the surgeon. Of course, the surgeon as is common practice manually sets the required generator parameters such as blend, cut, coag, power level, monopolar, bipolar, etc. Thus an effective surgical instrument is provided that responds to the load 12 imposed during a procedure.

The root mean square to direct current converter 26 for the summation value and the root mean square to direct current converter 28 for the differential value are useful as individual inputs 27 and 29 through analog to digital converters 30 and 31, to a microcontroller 32 with band limited signal processing capabilities. It is important to note the advantage of the high frequency power monitoring circuit 10 resides in the fact that the length and reactance of the active and return conductors 14 and 15, respectively are insignificant to the determination of the root mean square value of the actual power applied to the load 12. Wherefore, the use of different cord sets with this circuit has no ill effects on the performance or operation of the electrosurgical generator 11.

A feedback circuit 33 connects to the electrosurgical generator 11 for modifying the output thereof. The first and second adders 19 and 23, respectively, determine the instantaneous sum and difference of the voltage and the current in the active and return conductors, 14 and 15, respectively. Root mean square to direct current converters 26 and 28 provide the root mean square values 27 and 29 of the summation signal and differential signal 22 and 25, respectively, to the microprocessor 32. The microprocessor 32 can periodically receive and square the root mean square summation and root mean square differential values for calculation in the formula. Those squared values are subtracted, i.e. the differential from the summation, and the result therefrom is divided by four to provide an indication of instantaneous load 12 for use in the feedback circuit 33 to control the output of the electrosurgical generator 11 in real time.

The inductive pick up 17 for current flowing through at least one of the active or return conductors 14 or 15, respectively, of the output from the electrosurgical generator 11 is located along either the active conductor 14 or the return conductor 15 but is shown along active conductor 14 in FIG. 1. The inductive pick up 18 for the inverse of current flowing through the one active or return conductor 14 or 15 of the electrosurgical generator 11 output is located along either the active or return conductors 14 or 15, respectively, but is shown in FIG. 1 along active conductor 14. The electrosurgical generator 11 could have an internal diagnostic circuit which relates load impedance 12 and output response during operation to a look up table or an algorithm programmed in the microprocessor 32 for obtaining a correction to automatically calibrate the response and operation of the high frequency power monitoring circuit 10.

A self-operating desiccation regulator is connected to the electrosurgical generator 11 output to in response to impedance shut off output when the load impedance 12 is at a level preset in the microprocessor 32. An inductive pick up 16 for voltage between the active and return conductors 14 and 15, respectively, is connected to a root mean square to direct current converter 26 to provide a measure of the root mean square of the voltage. The microprocessor 12 is programmed to find the phase angle between voltage and current. An inductive pick up 16 for voltage between the active and return conductors 14 and 15, respectively is connected to a root mean square to direct current converter for the voltage to provide a measure of the root mean square of the voltage and the microprocessor 32 is programmed to find the length of a controlled capacitance cable.

FIG. 1 is a schematic diagram of the preferred high frequency power monitoring circuit 10 shown as blocks to represent the components thereof for use with the electrosurgical generator 11 applied to achieve an electrosurgical effect. There are four signal buffer/amplifiers designated 36, 37, 38, and 39 in FIG. 1. These signal buffer/amplifiers 36, 37, 38 and 39 are readily available "off the shelf" from many semiconductor manufacturers. For example, a preferred signal buffer/amplifier is the MC34084 from Motorola Semiconductor, Inc. of Phoenix, Ariz. The purpose of these signal buffer/amplifiers 36, 37, 38 and 39 in the high frequency power monitoring circuit 10 is to provide a low impedance output corresponding to the transducer outputs. These low impedance outputs prevent the signals in the high frequency power monitoring circuit 10 from interacting with one another.

The inductive pick up in-phase current sensor 17 is typically a transformer for sensing the in-phase current from the electrosurgical generator 11 active output 14 or electrosurgical generator 11 return 15. A summing node 22 is a point in the high frequency monitoring circuit 10 that has a ground-referenced voltage that is proportional to the instantaneous sum of the current and voltage signals. The root mean square to direct current converter 26 is preferably a monolithic semiconductor device which is available "off the shelf" from many manufacturers. An example of such a component is the AD637 from Analog Devices, Inc. of Norwood, Mass. The purpose of the root mean square to direct current converter 26 is to change a time-varying alternating current input signal to its equivalent direct current output.

The inductive pick up voltage transducer 16 is a transformer used in the high frequency monitoring circuit 10 to measure the electrosurgical generator 11 output voltage. The inductive pick up out-of-phase current sensor 18 is preferably a transformer that provides a voltage proportional to the output current of the electrosurgical generator 11. This output current is inverse, i.e. 180 degrees out of phase with the inductive pick up in-phase current sensor transformer 17. In other words, this wave form is the inverse or negative of that which is provided by the inductive pick up in-phase current sensor transformer 17. A differencing node 25 in the high frequency monitoring circuit 10 is a point that provides a ground-referenced voltage which is proportional to the instantaneous difference of the current and voltage signals.

The root mean square to direct current converter 28 is in the preferred embodiment a monolithic semiconductor device which is available "off the shelf" from many manufacturers. An example of such a component is the AD637 from Analog Devices, Inc. The purpose of the root mean square to direct current converter 28 is to change a time-varying alternating current input to the equivalent direct current output. The analog to digital converter 31 converts the analog input voltage into a digital word. It can be a discrete converter or integrated into the microprocessor 32 at the choice of the designer and consistent with the needs of the specific application.

A method for monitoring high frequency power from the electrosurgical generator 11 applied to a load 12 to achieve an electrosurgical effect with the step of connecting an electrosurgical generator 11 output to active and return conductors 14 and 15, respectively. The further step of connecting the inductive pick up 16 for voltage between the conductors 14 and 15, respectively of the electrosurgical generator 11 is included. Another step connects the inductive pick up 17 for current flowing through at least one of the active or return conductors 14 or 15, respectively of the output from the electrosurgical generator 11. The method has an added step of connecting the inductive pick up 18 for the inverse of current flowing through the one active or return conductor 14 or 15 of the electrosurgical generator 11 output. A step includes computing with the first adder circuit 19 the instantaneous inductively picked up voltage 20 with the instantaneously inductively picked up current 21 to provide a sum at summing node 22 indicative instantaneously thereof follows. The additional step of computing with a second adder circuit 23 the inductively picked up voltage 20 and the inverse of the instantaneously derived 24 current provides a differential value at differencing node 25 thereof. Converting a root mean square to direct current for the summation value at node 22 provides a signal of the instantaneous value of the summation as the root mean square summation value 27. Then the step of converting a root mean square to direct current for the differential value at node 25 provides a signal of the instantaneous value of the differential as the root mean square differential value 29. Thereafter, the step of receiving in a microprocessor 32 periodically the root mean square summation 27 and root mean square differential 29 values is employed. The method then includes the step of squaring those root mean square summation and differential values for application to the formula wherein the squared root mean square summation values have subtracted therefrom the squared root mean square differential values. Finally, the step of dividing the result therefrom by four to provide the root mean square value of the actual power applied to the load 12 is followed.

The step of the methods applies the root mean square to direct current converter for the summation 27 and differential 29 values to a microcontroller 32 with band limited signal processing capabilities. The step of determining the root mean square value of the actual power applied to the load 12 independently of the length and impedance of the active and return conductors 14 and 15, respectively is followed. Then the steps of connecting feedback circuit 33 to the electrosurgical generator 11 for modifying the output thereof and determining with the first and second adders 19 and 23 the root mean square value of the actual power applied to the load 12 in real time so the microprocessor 32 can periodically receive the root mean square summation 27 and root mean square differential 29 values and square those values for calculation wherein the result of subtracting the squared differential from the squared summation can be divided by four provides an indication of load 12 for use in the feedback circuit 33 to control the output of the electrosurgical generator 11.

The method has the step of locating the inductive pick up for current 17 flowing through at least one of the active or return conductors 14 or 15, respectively along the active conductor 14 or the return conductor 15. The step of locating the inductive pick up for the inverse of current 18 flowing through at least one of the active or return conductors 14 or 15, respectively along the active conductor 14 or the return conductor 15 is practiced. The step of providing in the electrosurgical generator 11 an internal diagnostic circuit which relates load impedance 12 and output response during operation to a look up table or an algorithm programmed in the microprocessor 32 for obtaining a correction to automatically calibrate the response and operation of the high frequency power monitoring circuit 10 is performed.

The step of connecting a self-operating desiccation regulator to the electrosurgical generator 11 output to in response to impedance shut off output when the impedance is at a level preset in the microprocessor 32 follows. The steps of connecting an inductive pick up 16 for voltage between the active and return conductors 14 and 15, respectively to the root mean square to direct current converter 26 for the voltage and thereby providing a measure of the root mean square of the voltage and the microprocessor 32 is programmed for finding the phase angle between voltage and current perhaps come thereafter. The steps of connecting the inductive pick up 16 for voltage between the active and return the conductors 14 and 15, respectively to a root mean square to direct current converter 28 for the voltage and thereby providing a measure of the root mean square of the voltage and the microprocessor is programmed for finding the length of a controlled capacitance cable may be a part of the method.

To determine the actual power delivered to the load 12, the microprocessor 32 performs the following calculation:

$$\frac{sum_{rms}(t,\theta)^2 - diff_{rms}(t,\theta)^2}{4} = i(t,\theta)_{rms}v(t,\theta)_{rms}\cos(\theta)$$

in which the RMS value of the sum is defined by the RMS value of the instantaneous sum of the voltage and current wave forms:

$$sum_{rms}(t,\theta) = \{v(t,\theta) + i(t,\theta)\}_{rms}$$

and the RMS value of the difference is defined by the RMS value of the instantaneous difference between the voltage and current wave forms:

$$diff_{rms}(t,\theta) = \{v(t,\theta) - i(t,\theta)\}_{rms}$$

The voltage signal is given by:

$$v(t,\theta) = k_v \sin(t)$$

where $k_v$ is the voltage amplitude.

The current signal is given by:

$$i(t,\theta) = k_i \sin(t+\theta)$$

Where $k_i$ is the amplitude of the current and $\theta$ is the angle by which the current is out of phase with the voltage.

The definition of the RMS value of f(x) over time period T is given by:

$$f(x)_{rms} = \sqrt{\frac{1}{T}\int_0^T f(x)^2 dx}$$

What is claimed is:

1. A high frequency power monitoring circuit for an electrosurgical generator applied to a load to achieve an electrosurgical effect comprising:
    a source of high frequency electrosurgical energy including an electrosurgical generator and its active and return conductors connected to the output thereof;
    an inductive pick up for voltage connected between the conductors of the electrosurgical generator;
    an inductive pick up for current flowing through at least one of the conductors of the output from the electrosurgical generator;
    an inductive pick up for the inverse of current flowing through the one conductor of the electrosurgical generator output;
    a first adder circuit for computing the instantaneous inductively picked up voltage with the instantaneously inductively picked up current to provide a sum indicative instantaneously thereof;
    a second adder circuit for computing the inductively picked up voltage and the inverse of the instantaneously derived current providing a differential value thereof;
    a root mean square to direct current converter for the summation value to provide a signal of the instantaneous value of the summation as a root mean square summation value;
    a root mean square to direct current converter for the differential value to provide a signal of the instantaneous value of the differential as a root mean square differential value, and
    a microprocessor to periodically receive the root mean square summation and root mean square differential values and square those instantaneous root mean square summation and differential values for application to a formula wherein the squared root mean square summation values have subtracted therefrom the squared root mean square differential values so the result therefrom can be divided by four to provide the root mean square value of the actual power applied to the load.

2. The high frequency power monitoring circuit for an electrosurgical generator of claim 1 wherein the root mean square to direct current converter for the summation value and the root mean square to direct current converter for the differential value are each inputs to a microcontroller with band limited signal processing capabilities.

3. The high frequency power monitoring circuit for an electrosurgical generator of claim 1 wherein a feedback circuit connected to the electrosurgical generator for modifying the output thereof and the first and second adders determining the root mean square value of the actual power applied to the load in real time so the microprocessor can periodically receive the root mean square summation and root means square differential values and square those values for calculation in the formula so the result therefrom can be divided by four to provide an indication of load for use in the feedback circuit to control the output of the electrosurgical generator.

4. The high frequency power monitoring circuit for an electrosurgical generator of claim 1 wherein the inductive pick up for current flowing through at least one of the conductors of the output from the electrosurgical generator is located along the active conductor or the return conductor.

5. The high frequency power monitoring circuit for an electrosurgical generator of claim 1 wherein the inductive pick up for the inverse of current flowing through the one conductor of the electrosurgical generator output is located along the active or return conductors.

6. The high frequency power monitoring circuit for an electrosurgical generator of claim 1 wherein the electrosurgical generator has an internal diagnostic circuit which relates impedance load and output response during operation to a look up table or an algorithm programmed in the microprocessor for obtaining a correction to automatically calibrate the response and operation of the high frequency power monitoring circuit.

7. The high frequency power monitoring circuit for an electrosurgical generator of claim 1 wherein a tissue load responsive regulator is connected to the electrosurgical generator output to in response to impedance shut off output when the impedance is at a level preset in the microprocessor.

8. The high frequency power monitoring circuit for an electrosurgical generator of claim 1 wherein an inductive pick up for voltage between the active and return the conductors is connected to a root mean square to direct current converter for the voltage to provide a measure of the root mean square of the voltage and the microprocessor is programmed to find the phase angle between voltage and current.

9. The high frequency power monitoring circuit for an electrosurgical generator of claim 1 wherein an inductive pick up for voltage between the active and return the conductors is connected to a root mean square to direct current converter for the voltage to provide a measure of the root mean square of the voltage and the microprocessor is programmed to find the length of a controlled capacitance cable.

10. A high frequency power monitoring circuit for an electrosurgical generator applied to a load to achieve an electrosurgical effect comprising:
    a source of high frequency electrosurgical energy including an electrosurgical generator and its active and return conductors connected to the output thereof;
    an inductive pick up for voltage connected between the conductors of the electrosurgical generator;
    an inductive pick up for current flowing through at least one of the conductors of the output from the electrosurgical generator is located along the active conductor or the return conductor;
    an inductive pick up for the inverse of current flowing through the one conductor of the electrosurgical generator output is located along the active or return conductors;
    a first adder circuit for computing the instantaneous inductively picked up voltage with the instantaneously inductively picked up current to provide a sum indicative instantaneously thereof;
    a second adder circuit for computing the inductively picked up voltage and the inverse of the instantaneously derived current providing a differential value thereof;

a root mean square to direct current converter for the summation value to provide a signal of the instantaneous value of the summation as a root mean square summation value;

a root mean square to direct current converter for the differential value to provide a signal of the instantaneous value of the differential as a root mean square differential value;

a microcontroller with band limited signal processing capabilities so the root mean square to direct current converter for the summation value and the root mean square to direct current converter for the differential value are each inputs to the microcontroller;

a microprocessor to periodically receive the root mean square summation and root mean square differential values and square those instantaneous root mean square summation and differential values for application to a formula wherein the squared root mean square summation values have subtracted therefrom the squared root mean square differential values so the result therefrom can be divided by four to provide the root mean square value of the actual power applied to the load;

a tissue load responsive regulator is connected to the electrosurgical generator output to in response to impedance shut off output when the impedance is at a level preset in the microprocessor;

an internal diagnostic circuit which relates impedance load and output response during operation to a look up table or an algorithm programmed in the microprocessor for obtaining a correction to automatically calibrate the response and operation of the high frequency power monitoring circuit, and a feedback circuit connected to the electrosurgical generator for modifying the output thereof and the first and second adders determining the root mean square value of the actual power applied to the load in real time so the microprocessor can periodically receive the root mean square summation and root means square differential values and square those values for calculation in the formula for the result therefrom to be divided by four to provide an indication of load for use in the feedback circuit to control the output of the electrosurgical generator so the length and impedance of the active and return conductors are insignificant to the determination of the root mean square value of the actual power applied to the load.

11. A method for monitoring high frequency power from an electrosurgical generator applied to a load to achieve an electrosurgical effect with the following steps:

connecting an electrosurgical generator output to active and return conductors;

connecting an inductive pick up for voltage between the conductors of the electrosurgical generator;

connecting an inductive pick up for current flowing through at least one of the conductors of the output from the electrosurgical generator;

connecting an inductive pick up for the inverse of current flowing through the one conductor of the electrosurgical generator output;

computing with a first adder circuit the instantaneous inductively picked up voltage with the instantaneously inductively picked up current to provide a sum indicative instantaneously thereof;

computing with a second adder circuit the inductively picked up voltage and the inverse of the instantaneously derived current providing a differential value thereof;

converting a root mean square to direct current for the summation value to provide a signal of the instantaneous value of the summation as a root mean square summation value;

converting a root mean square to direct current for the differential value to provide a signal of the instantaneous value of the differential as a root mean square differential value, and receiving in a microprocessor periodically the root mean square summation and root mean square differential values;

squaring those instantaneous root mean square summation and differential values for application to a formula wherein the squared root mean square summation values have subtracted therefrom the squared root mean square differential values, and then dividing the result therefrom by four to provide the root mean square value of the actual power applied to the load.

12. The method of claim 11 with the step of applying the root mean square to direct current converter for the summation and differential values to a microcontroller with band limited signal processing capabilities.

13. The method of claim 11 with the step of determining the root mean square value of the actual power applied to the load independently of the length and impedance of the active and return conductors.

14. The method of claim 11 with the steps of connecting a feedback circuit to the electrosurgical generator for modifying the output thereof and determining with the first and second adders the root mean square value of the actual power applied to the load in real time so the microprocessor can periodically receive the root mean square summation and root mean square differential values and square those values for subtracting the squared differential values from the squared summation values so the result therefrom can be divided by four to provide an indication of load for use in the feedback circuit to control the output of the electrosurgical generator.

15. The method of claim 11 with the step of locating the inductive pick up for current flowing through at least one of the conductors along the active conductor or the return conductor.

16. The method of claim 11 with the step of locating the inductive pick up for the inverse of current flowing through at least one of the conductors along the active conductor or the return conductor.

17. The method of claim 11 with the step of providing in the electrosurgical generator an internal diagnostic circuit which relates impedance load and output response during operation to a look up table or an algorithm programmed in the microprocessor for obtaining a correction to automatically calibrate the response and operation of the high frequency power monitoring circuit.

18. The method of claim 11 with the step of connecting a tissue load responsive regulator to the electrosurgical generator output to in response to impedance shut off output when the impedance is at a level preset in the microprocessor.

19. The method of claim 11 with the steps of connecting an inductive pick up for voltage between the active and return the conductors to a root mean square to direct current converter for the voltage and thereby providing a measure of the root mean square of the voltage and the microprocessor is programmed for finding the phase angle between voltage and current.

20. The method of claim 11 with the steps of connecting an inductive pick up for voltage between the active and return the conductors to a root mean square to direct current converter for the voltage and thereby providing a measure of the root mean square of the voltage and the microprocessor is programmed for finding the length of a controlled capacitance cable.

* * * * *